United States Patent
Wyart et al.

(10) Patent No.: US 10,526,340 B2
(45) Date of Patent: Jan. 7, 2020

(54) PROCESS FOR MANUFACTURING DIANHYDROHEXITOL CRYSTALS WITH A STEP OF EVAPORATIVE CRYSTALLIZATION OF THE FIRST CRYSTALLIZATION MOTHER LIQUORS

(71) Applicant: ROQUETTE FRERES, Lestrem (FR)

(72) Inventors: Hervé Wyart, Cuinchy (FR); Thomas Lesur, Haubourdin (FR); Mathias Ibert, La Chapelle d'Armentieres (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 16/095,300

(22) PCT Filed: Apr. 21, 2017

(86) PCT No.: PCT/FR2017/050947
§ 371 (c)(1),
(2) Date: Oct. 19, 2018

(87) PCT Pub. No.: WO2017/187058
PCT Pub. Date: Nov. 2, 2017

(65) Prior Publication Data
US 2019/0135826 A1    May 9, 2019

(30) Foreign Application Priority Data
Apr. 25, 2016 (FR) .................................. 16 53619

(51) Int. Cl.
C07D 493/00    (2006.01)
C07D 493/04    (2006.01)

(52) U.S. Cl.
CPC .................................. C07D 493/04 (2013.01)

(58) Field of Classification Search
CPC .................................................. C07D 493/04

USPC .......................................................... 549/464
See application file for complete search history.

(56) References Cited

U.S. PATENT DOCUMENTS

| 4,408,061 A | 10/1983 | Salzburg et al. |
| 4,861,513 A | 8/1989 | Lueders et al. |
| 2008/0213439 A1 | 9/2008 | Fuertes |
| 2015/0252054 A1 | 9/2015 | Ryu et al. |

FOREIGN PATENT DOCUMENTS

| CA | 1 178 288 A | 11/1984 |
| EP | 0 323 994 A1 | 7/1989 |
| EP | 1 446 373 A1 | 8/2004 |
| EP | 2 918 572 A1 | 9/2015 |
| GB | 613 444 A | 11/1948 |
| KR | 10-2014-0059904 A | 5/2014 |
| KR | 10-2014-0059906 A | 5/2014 |
| KR | 10-2014-0080748 A | 7/2014 |
| WO | 00 / 14081 A1 | 3/2000 |
| WO | 2014 073848 A1 | 5/2014 |

OTHER PUBLICATIONS

Wikipedia, Crystallization, Oct. 2015, p. 1-12. (Year: 2015).*
Jul. 7, 2017 International Search Report issued in International Patent Application No. PCT/FR2017/050947.

* cited by examiner

*Primary Examiner* — Taylor V Oh
(74) *Attorney, Agent, or Firm* — Oliff PLC

(57) ABSTRACT

A process for manufacturing crystals of 1,4:3,6-dianhydrohexitols, by manufacturing a solution of an internal dehydration product of at least one hexitol, distilling the solution, crystallizing, and wherein the crystallization mother liquors undergo a step of evaporative crystallization. Unlike the prior art processes that seek to recycle the crystallization mother liquors, evaporative crystallization economically and efficiently replaces the succession of steps consisting of at least one concentration, then at least one step of purification by distillation, chromatography, or crystallization.

12 Claims, No Drawings

PROCESS FOR MANUFACTURING DIANHYDROHEXITOL CRYSTALS WITH A STEP OF EVAPORATIVE CRYSTALLIZATION OF THE FIRST CRYSTALLIZATION MOTHER LIQUORS

The present invention relates to a process for producing 1,4:3,6-dianhydrohexitol crystals, by producing a solution of an internal dehydration product of at least one hexitol, distilling said solution and crystallizing, and characterized in that the crystallization mother liquors undergo an evaporative crystallization step. Unlike the prior art processes that seek to exploit the crystallization mother liquors, evaporative crystallization economically and efficiently replaces the succession of steps consisting of at least one concentration, then at least one step of purification by distillation, chromatography, or crystallization.

The exploitation of renewable biological resources has become a major ecological and economic imperative, in the face of the depletion and of the increase in costs of fossil materials such as petroleum. The development of 1,4:3,6-dianhydrohexitols for which there is a strong development potential, in particular in the pharmaceutical field, in the production of chemical synthesis intermediates and in the plastics sector, falls within this context.

These products, also referred to as isohexides, are obtained by internal dehydration of hydrogenated $C_6$ sugars (hexitols) such as sorbitol, mannitol and iditol. In the present patent application, the term "dianhydrohexitols" encompasses isosorbide (1,4:3,6-dianhydrosorbitol), isomannide (1,4:3,6-dianhydromannitol) and isoidide (1,4:3,6-dianhydroiditol) of the following formulae, and also mixtures of these products:

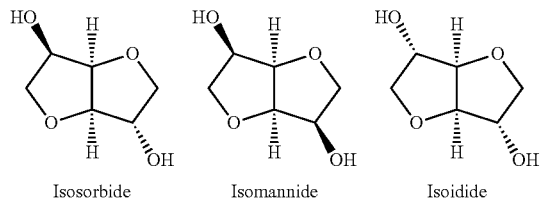

Isosorbide     Isomannide     Isoidide

This dehydration step is always followed, industrially, by a purification step, in particular by distillation. This process is today well known to those skilled in the art, and in particular described in documents WO 00/14081, U.S. Pat. No. 4,408,061 and EP 0 323 994. The Applicant Company has itself widely reported and exemplified it, in particular in patent application EP 1 446 373.

The isosorbide distillate thus obtained is then crystallized. To do this, it is generally dissolved in a solvent, such as 2-propanol (or isopropanol), at a temperature of about 60° C., so as to obtain a solution containing approximately 75% solids. This solution is then slowly cooled, over a time ranging from 2 to 10 hours, until a temperature of about 10° C. is reached. A recrystallized isosorbide initiator is added when the temperature is about 40° C. in order to initiate the crystallization. The crystals are then drained in a centrifuge and washed with a small amount of 2-propanol. After vacuum drying, said crystals are optionally redissolved in water so as to obtain an aqueous solution of isosorbide that can be subjected to additional decoloring and/or demineralization treatments.

The draining step results in the formation of 2 streams: the main stream which consists of a stream of isosorbide crystals (the dry weight content of isosorbide of which is about 98% of its total weight) and a secondary stream also referred to as "mother liquors", the isosorbide richness of which is much lower (the isosorbide dry weight content thereof is about 30% of its total weight).

With the constant view of improving the yield of their industrial process, those skilled in the art have sought to exploit the stream of mother liquors so as to purify it and/or concentrate it so as to either reintroduce it at the initial distillation step, or to exploit it as it is if it contains crystallized isosorbide in sufficient amount.

In this respect, a known document is document KR 2014-005 9906, which describes a process consisting in dehydrating sorbitol, in distilling the isosorbide obtained, and in then crystallizing the distillate from acetone. The mother liquors are then concentrated to dryness in an evaporator, and undergo crystallization after being redissolved in acetone, before being reintroduced at the initial step of crystallization of the distillate. The final isosorbide purity is then 99.7%, the crystallization yield is 91.9% and the overall yield of the process is equal to 68.7% according to example 1 of this patent application.

Document KR 2014-0059904 describes, for its part, a process which is identical up to the mother liquor treatment step. Said mother liquors are concentrated to dryness by evaporation, then distilled, before being reintroduced at the initial step of crystallization of the distillate. The final isosorbide purity is then 99.8%, the crystallization yield is 92.1% and the overall yield of the process is equal to 71.0% according to example 1 of this patent application.

Document KR 2014-0080748 reiterates the upstream part of the process described above. In this case, the mother liquors are concentrated to dryness still by evaporation, redissolved in water, then purified by simulated moving bed (SMB) chromatography, before undergoing a further concentration step. This stream is reintroduced at the initial step of crystallization of the distillate. The final isosorbide purity is then 99.5%, the crystallization yield is 92.0% and the overall yield of the process is equal to 75.0% according to example 1 of this patent application.

Finally, document WO 2014/073848, which relies on the same initial steps, describes the concentration to dryness of the mother liquors and the reintroduction thereof upstream of the initial crystallization step, that is to say in the initial distillate. This new distillate then undergoes the initial crystallization step once again. The final isosorbide purity is then 99.7%, the crystallization yield is 88.0% and the overall yield of the process is equal to 67.4% according to example 1 of this patent application.

All of the abovementioned processes nevertheless have the drawback of carrying out at least 2 steps for treating the mother liquor stream, this being before reintroducing it at the top of the process, either into the distillate for crystallization, or at the very level of the initial distillation step. These steps consist of at least one step of concentration to dryness by evaporation, which consumes very high amounts of energy, and another step of purification consisting of a crystallization, a chromatographic separation or a distillation. The cost associated with carrying out at least 2 additional steps is an economic impairment to the industrial implementation of the corresponding process.

Working to optimize its process for producing 1,4:3,6-dianhydrohexitol crystals, the Applicant has managed, after numerous studies, to develop a process which is particularly economical and efficient in terms of its yield. Said process is based in particular on an evaporative crystallization step carried out on the mother liquors resulting from the first crystallization, in place of the (at least) 2 steps described in the prior art.

Surprisingly, since not described in the prior art, the recourse to evaporative crystallization on the mother liquor stream limits the number of treatment steps, while the same time resulting in particularly high yields in terms of the crystallization, of the overall process, and with a particularly high isosorbide purity.

This process for producing 1,4:3,6-dianhydrohexitol crystals comprises the steps of:
  a) providing a solution of an internal dehydration product of a hexitol,
  b) distilling the solution resulting from step a),
  c) crystallizing the distillate resulting from step b),
  d) draining the crystals resulting from step c),
and subjecting the mother liquor stream resulting from the draining to an evaporative crystallization step e).

In the present application, the term "evaporative crystallization" denotes the combination of the steps of: concentrating by vacuum evaporation so as to form a concentrated and supersaturated solution which begins to crystallize, seeding the medium which consists of the supersaturated solution, crystallizing under partial vacuum so as to continue the crystallization process.

More specifically, this process for producing 1,4:3,6-dianhydrohexitol crystals comprises the steps of:
  a) providing a solution of an internal dehydration product of at least one hexitol,
  b) distilling the solution resulting from step a) so as to obtain a solution of at least one 1,4:3,6-dianhydrohexitol,
  c) crystallizing the 1,4:3,6-dianhydrohexitol resulting from step b),
  d) draining the 1,4:3,6-dianhydrohexitol crystals resulting from step c), which results in a crystal-rich stream (1) and a mother liquor stream (1 bis),
and is characterized in that all or a part of the mother liquor stream (1 bis) undergoes an evaporative crystallization step e) in the presence of solvent, which results in the formation of a solvent stream (2) and in the formation of a stream rich in 1,4:3,6-dianhydrohexitol crystals (2 bis).

More specifically, the crystallization according to step c) results in a stream rich in 1,4:3,6-dianhydrohexitol crystals. These crystals are drained in step d), which makes it possible to release, on the one hand, a main stream (1) rich in 1,4:3,6-dianhydrohexitol crystals and, on the other hand, a mother liquor stream (1 bis). The crystals of the main stream (1) are recovered and constitute the exploitable final product resulting from the process according to the present invention.

Thus, according to a first variant, the process according to the invention is characterized in that all of the mother liquor stream (1 bis) resulting from the draining step d) undergoes an evaporative crystallization step e).

In a second variant, the process according to the invention is characterized in that a part of the mother liquor stream (1 bis) resulting from the draining step d) undergoes an evaporative crystallization step e), preferably from 50% to 99.9% by weight of said stream undergoing the evaporative crystallization step, from 0.1% to 50% by weight of said stream being reintroduced into the distillate at the crystallization step c).

The evaporative crystallization step e), carried out in an evaporative crystallizer and in the presence of solvent, preferentially a linear or branched aliphatic alcohol, allows the distillation of said solvent and therefore the formation of a solvent stream (2), and also the formation of a stream rich in 1,4:3,6-dianhydrohexitol crystals (2 bis) after having reached a solids content corresponding to a degree of 1,4:3,6-dianhydrohexitol supersaturation which is sufficient to generate crystallization. This degree of supersaturation is generally reached starting from a solids content of 75%. Preferably, the solvent is chosen from a linear or branched $C_1$-$C_4$ aliphatic alcohol, preferentially from methanol, ethanol, propylene glycol and isopropanol, isopropanol being the most preferred solvent.

The 1,4:3,6-dianhydrohexitol supersaturation of a 1,4:3,6-dianhydrohexitol solution, at a given temperature, is defined as the ratio of the mass of 1,4:3,6-dianhydrohexitol to the mass of solvent of the solution, related back to the mass of 1,4:3,6-dianhydrohexitol to the mass of solvent of the saturated solution in the pure state. A degree of supersaturation of 1 therefore corresponds to a saturated solution of 1,4:3,6-dianhydrohexitol. A degree of supersaturation of less than 1 corresponds to a solution for which crystallization is not possible.

The process according to the invention can also comprise an additional step, said step consisting in that the crystals of the stream rich in 1,4:3,6-dianhydrohexitol crystals (2 bis) resulting from the evaporative crystallization step e) are drained at a step f), which results in the formation, on the one hand, of a main stream (3) rich in 1,4:3,6-dianhydrohexitol crystals and, on the other hand, in the formation of a mother liquor stream (3 bis).

According to one variant of the process, this main stream (3) is reintroduced into the distillate at step c). According to another variant, the crystals are recovered from the main stream (3) and constitute the exploitable final product resulting from the process according to the present invention, in the same way as the crystals recovered from the main stream (1).

As regards the mother liquor stream (3 bis), it is, according to one variant of the invention, reintroduced at the evaporative crystallization step e), or reintroduced, according to another variant, further upstream of the overall process, after having removed therefrom the crystallization solvent, and more specifically at step a) of providing the initial solution of the internal dehydration product of the hexitol and/or at step b) of distilling the solution of the internal dehydration product of the hexitol.

According to one particular mode, the entire process which is the subject of the present invention can be carried out continuously.

In practice, step a) consists in preparing a solution of an internal dehydration product of a hexitol. This solution has a mass concentration of 1,4:3,6-dianhydrohexitol of between 65% and 80%, preferentially between 70% and 75%.

This solution is preferentially obtained by removal of the water from an initial aqueous solution containing at least one hexitol. The removal of the water is performed via any means well known to those skilled in the art, especially by heating, in particular by vacuum distillation. The initial aqueous solution is, for example, a product sold by the Applicant under the name Neosorb.

The solution containing at least one hexitol is also characterized in that the hexitol is chosen from sorbitol, mannitol and iditol, and mixtures thereof, and is preferentially sorbitol.

Said hexitol is then dehydrated so as to obtain a 1,4:3,6-dianhydrohexitol.

This step is in no way limiting for the process that is the subject of the present patent application. It may be carried out according to any of the processes that are well known to those skilled in the art. In this respect, mention may be made of patent CA 1 178 288, which recalls on page 14, lines 3-8 thereof that it is recommended to perform the dehydration reaction per se under an atmosphere of an inert gas to avoid oxidation reactions, especially when relatively high reaction temperatures and long reaction times are envisioned. One variant according to the present invention thus consists in performing this dehydration step under an atmosphere of an inert gas.

U.S. Pat. No. 4,861,513 describes a sorbitol dehydration reaction performed in the simultaneous presence of an inert gas (nitrogen) and of a reducing agent (sodium hypophosphite) for the purpose of preparing mixtures of particular polyols, which have a low content (10 to 26%) of dianhydrosorbitol. The abovementioned patent GB 613 444, for its part, describes the production, by dehydration in water/solvent medium, of an isosorbide composition which is then subjected to a distillation treatment and then recrystallization from an alcohol/ether mixture.

Preferably, the conditions for performing this dehydration step are the following: the solution containing the hexitol obtained after removal of the water from the initial solution is introduced into a reactor. Simultaneously, before or after the introduction of the hexitol solution, the dehydration catalyst is introduced into the reactor. This catalyst may be of any type, provided that it allows the dehydration of the hexitol in the subsequent step. This catalyst may be a heterogeneous catalyst or a homogeneous catalyst. It may be an acid catalyst, in particular a strong acid catalyst, or ion-exchange resins, in particular acidic cation-exchange resins, or acidic zeolite-type catalysts. The acid catalyst may especially be sulfuric acid, hydrochloric acid, para-toluenesulfonic acid, phosphoric acid or methanesulfonic acid. Sulfuric acid is a catalyst that is particularly preferred for the manufacture of the composition according to the invention.

The acidic cation exchange resin may be a sulfonated polystyrene resin such as the AG50W-X12 resin from Bio-Rad. The acidic zeolite may be a beta-zeolite.

The dehydration catalyst is introduced in amounts which allow the dehydration step to be carried out. In particular, when sulfuric acid is used, it is preferable to use amounts of less than 2% by weight relative to the total weight of hexitol, preferably less than 1.5%, most preferentially less than 1.2%.

The dehydration step may be performed under vacuum, under a stream of an inert gas, for example nitrogen, or else under pressure in an autoclave, these three methods making it possible to facilitate the removal of the water and thus to shift the reaction equilibrium.

To perform the dehydration step, it is necessary to provide the reactor with heat. This amount of heat required depends mainly on the nature and on the amount of catalyst used and, to a lesser extent, on the pressure conditions in the reactor during the dehydration step. To provide the required heat, the temperature inside the reactor and at which the dehydration reaction is performed may range from 110° C. to 400° C. depending on the catalyst used. For example, when 1% by mass of sulfuric acid is used, relative to the mass of hexitol introduced, a temperature greater than or equal to 135° C., advantageously greater than or equal to 150° C., is preferably used. Advantageously, the temperature remains below 300° C.

On conclusion of the dehydration step, when a homogeneous acid catalyst is used, a step of neutralizing the catalyst is preferably performed.

Step b) consists in distilling the solution resulting from step a). This distillation is performed according to any technique available to those skilled in the art. This step can be carried out in any type of still which allows the dianhydrohexitols to be isolated. This step is carried out under vacuum, temperature and time conditions which allow the dianhydrohexitols to be isolated from the rest of the constituents of the composition. By way of example, the distillation can be carried out, until the dianhydrohexitol no longer distills, at 50 mbar and at a temperature of 250° C. or else at 5 mbar and at a temperature of 200° C.

In this step, the 1,4:3,6-dianhydrohexitol is isosorbide (1,4:3,6-dianhydrosorbitol), isomannide (1,4:3,6-dianhydromannitol), isoidide (1,4:3,6-dianhydroiditol) or mixtures thereof, and is preferentially isosorbide.

Step c) consists in crystallizing the product resulting from step b). This step is not limiting and can be performed according to any of the processes known to those skilled in the art. For example, the distillate resulting from step b) is dissolved in a solvent of the linear or branched aliphatic alcohol type, preferentially a $C_1$-$C_4$ linear or branched aliphatic alcohol, very preferentially methanol, ethanol, propylene glycol and isopropanol, isopropanol being the most preferred solvent. The solids content thereof is then between 50% and 80% of its total weight, and is preferentially approximately 70%. This solution is then slowly cooled, over a period of time ranging from 2 to 10 hours, and preferentially about 5 hours, until a temperature of between 5° C. and 25° C., preferentially between 10° C. and 20° C., is reached. A recrystallized 1,4:3,6-dianhydrohexitol initiator is added when the temperature is about 40° C., in order to initiate the crystallization. The crystals are then drained in a centrifuge and washed with a small amount of isopropanol (or 2-propanol).

The draining of the crystals makes it possible to release, on the one hand, a main stream (1) rich in 1,4:3,6-dianhydrohexitol crystals and a mother liquor stream (1 bis). Their respective solids mass contents are, on the one hand, between 95% and 99% and, on the other hand, between 30% and 35%, and their 1,4:3,6-dianhydrohexitol richnesses (or dry weight contents of 1,4:3,6-dianhydrohexitols) are, on the one hand, between 94.9% and 98.9% and, on the other hand, between 27% and 32%.

An evaporative crystallization step is then carried out on the mother liquors (1 bis). This is carried out by evaporation in an evaporative crystallizer, by introducing saturated vapor through a heat exchanger placed either in said evaporative crystallizer, or in a recirculation loop. A degree of supersaturation sufficient to generate crystallization is thus created.

In the examples of the present application, it is demonstrated that the use of isopropanol, which corresponds to the preferred variant of the invention, makes it possible to implement conditions that are absolutely "mild" in terms of temperature and pressure. Isopropanol in fact has the advantage of being able to be used under temperature conditions which are close to ambient and vacuum conditions which are not very strong.

The supersaturated solution is then seeded by introducing at least one crystalline seed. Said seed consists of a 1,4:3,6-dianhydrohexitol initiator and can be in dispersed form, in a linear or branched aliphatic alcohol, preferentially a $C_1$-$C_4$ linear or branched aliphatic alcohol, very preferentially chosen from methanol, ethanol, propylene glycol and isopropanol, isopropanol being the most preferred solvent.

The crystallization is carried out under partial vacuum which is kept constant. The evaporation is carried out in such a way that vigorous and well-controlled stirring of the supersaturated solution is obtained in the evaporative crystallizer. The solvent which evaporates from said solution will in fact create a pumping phenomenon that vigorously stirs the solution. This phenomenon makes it possible to stir the solution with a much greater amplitude than that which would be generated by mechanical stirring. The solvent evaporated off is then either eliminated from the evaporative crystallizer, or condensed therein. The solids content of the solution at the inlet of the evaporative crystallizer is also adjusted so as to obtain the amount of saturated vapor required and sufficient for the pumping.

The evaporative crystallization results in a solvent stream (2), preferentially an isopropanol stream, and a stream rich in 1,4:3,6-dianhydrohexitol crystals (2 bis). The solids mass content of the stream rich in 1,4:3,6-dianhydrohexitol crystals (2 bis) is between 75% and 90%, and the richness in 1,4:3,6-dianhydrohexitols (or dry weight content of 1,4:3, 6-dianhydrohexitols) is between 67.5% and 82.5%.

The crystals of the stream rich in 1,4:3,6-dianhydrohexitol crystals (2 bis) resulting from the evaporative crystallization step can then be drained (step f). This step f) makes it possible to release a main stream (3) rich in 1,4:3,6-dianhydrohexitol crystals and a mother liquor stream (3 bis). The respective solids mass contents of these two streams are, on the one hand, between 95% and 99% and, on the other hand, between 60% and 82%, and their 1,4:3,6-dianhydrohexitol richnesses (or dry weight contents of 1,4:3,6-dianhydrohexitols) are, on the one hand, between 94.5% and 98.8% and, on the other hand, between 48% and 68%.

EXAMPLES

Example 1

Step a)

10 kg of a sorbitol solution with a solids content of 70% (i.e. 7000 g dry) sold by the Applicant under the name Neosorb® 70/02, and 70 g of concentrated sulfuric acid, is introduced into a 10 l Schott brand glass reactor, equipped with a jacket fed with an oil-circulation thermostated bath, a stirring paddle, a thermometer, a distillation head combined with a condenser and a distillation receiver. The mixture obtained is heated under vacuum (pressure of approximately 100 mbar) for 5 hours so as to eliminate the water contained in the initial reaction medium and that originating from the sorbitol dehydration reaction. The reaction crude is then cooled to 100° C. and then neutralized with 110.4 g of a 50% (by weight) sodium hydroxide solution.

Step b)

The isosorbide composition neutralized in this way is then distilled under vacuum (pressure lower than 50 mbar). 3900 g of crude isosorbide distillate having a purity of 98.0%, measured by gas chromatography (GC), are obtained.

Step c)

The crude isosorbide distillate is then dissolved in isopropanol (or 2-propanol), at a temperature of 60° C., so as to obtain a solution with a 70% solids content (SC). This solution is transferred into an 8-liter stirred crystallizer equipped with a water-fed jacket, and is then slowly cooled, over a period of 5 hours, to a temperature of 20° C. At 40° C., the supersaturation of the solution is 1.23 and a recrystallized isosorbide initiator is added in order to bring about crystallization.

Step d)

At the end of the operation, the crystals are separated from the suspension obtained, in a centrifuge, and washed with 2-propanol. After vacuum drying, a main stream (1) containing 3125 g of dry isosorbide crystals having a purity equal to 99.9%, measured by GC, is obtained. The crystallization yield of isosorbide is 81.7%. The mother liquor stream (1 bis) (mass 2380 g) has a solids content of 32.5%, has an isosorbide purity of 90.4% measured by GC, relative to the solids content, and has a supersaturation equal to 0.27.

Step e)

The mother liquor stream (1 bis) is transferred into a 5-liter reactor equipped with a jacket fed by a thermostated water circulation bath, with a stirring blade, with a thermometer, and with a distillation head that is equipped with a valve associated with a reflux condenser and with a distillation receiver in order to carry out the evaporative crystallization step. The solution is heated at 40° C. under vacuum (pressure 100 mbar) in order to allow the distillation of the isopropanol. The vacuum is then gradually increased, which has the effect of gradually decreasing the temperature during the distillation of the isopropanol. When the temperature of the solution reaches 30° C., the pressure is 60 mbar, the solids content is 85% and the supersaturation is equal to 3.53. A recrystallized isosorbide initiator is added in order to bring about the crystallization. After having closed the valve at the distillation head, the vacuum is gradually increased, which has the effect of gradually decreasing the temperature while at the same time maintaining a constant solids content by total reflux of the isopropanol with boiling. When the pressure reaches 30 mbar, the temperature is 20° C. The distilled isopropanol stream (2) is 1470 g. The choice of isopropanol makes it possible to work under particularly "mild" conditions, as attested to by the temperature at the end of the crystallization.

Step f)

The crystals are separated from the suspension obtained (2 bis), in a centrifuge, and washed with 2-propanol. After vacuum drying, a main stream (3) containing 390 g of isosorbide crystals having a purity equal to 99.7%, measured by GC, is obtained. The evaporative crystallization yield of isosorbide is 55.5%. The streams (1) and (3) of crystals are combined and constitute a stream of 3515 g of isosorbide having a purity equal to 99.87% measured by GC. The overall crystallization yield relative to the crude isosorbide distillate used is equal to 90.1% by mass. The mother liquor stream (3 bis) is 510 g and has a solids content of 75.5% with a purity, measured by GC, of 80.8% relative to the solids content. This stream (3 bis) is then concentrated to dryness in order to recover the isopropanol, then stored with a view to it being reintegrated during a subsequent production, in step a) of the process.

Example 2

Example 1 is repeated up to step f).

At this level, the streams (1) and (3) are not combined as in example 1, but the main stream (3) resulting from step f) is entirely recycled to the crystallization step c). After draining and drying of the crystals as indicated in step d) of example 1, 3442 g of dry crystals having a purity equal to 99.95%, measured by GC, are obtained, with an overall crystallization yield, relative to the crude isosorbide distillate used, of 88.3% by weight.

Example 3

A continuous-mode operation is applied to the process according to the invention. Firstly, a crystallization is carried out according to example 1. After 5 hours, when the temperature of 20° C. is reached, the crystallizer is fed at a flow rate of 1000 g/h with a mixture of distillate of isosorbide and isopropanol having a solids content of 70%. A stream of crystals is continuously extracted from the crystallizer at a flow rate equivalent to the feed flow rate of mixture of distillate of isosorbide/isopropanol.

This stream is continuously separated on a centrifuge into a stream (1) rich in crystals (approximately 550 g/h dried, having a purity equal to 99.9%) and a mother liquor stream (1 bis). The stream (1 bis) having a flow rate approximately equal to 440 g/h is continuously introduced into an evaporative crystallizer and the vacuum and temperature conditions described in example 1 are applied, making it possible to evaporate off the isopropanol and to increase the solids content in order to bring about the crystallization of the crystals. When the solids content of 85% and the temperature of 20° C. are reached, a stream (2) with a flow rate of approximately 265 g/h of isopropanol distillate is obtained in an equilibrated system. A stream (2 bis) of crystals is continuously extracted from the crystallizer, making it possible to keep a constant level in the evaporative crystallizer, i.e. approximately 175 g/h.

This stream (2 bis) is continuously separated on a centrifuge into a stream (3) rich in crystals (approximately 70 g/h dried, having a purity equal to 99.6%) and a mother liquor stream (3 bis). The streams (1) and (3) of crystals are combined and constitute a stream of 620 g/h of isosorbide having a purity equal to 99.87% measured by GC. The overall crystallization yield relative to the continuous feed stream of crude isosorbide distillate is equal to 88.6% by mass. The mother liquor stream (3 bis) of approximately 105 g/h is concentrated to dryness in order to recover the isopropanol, then recycled to step b) of the process.

This example demonstrates that the process according to the invention adapts perfectly to a continuous operation, which is an asset in terms of cost-effectiveness of an industrial process.

Example 4

Example 3 is repeated up to the equilibration of the various feed and outlet streams of the 2 crystallizers. The stream of drained crystals (3) resulting from the evaporative crystallizer is then continuously reintroduced into the first crystallizer while decreasing accordingly the isosorbide distillate feed flow rate in order to keep the level in the crystallizer constant. The crystal stream (1) resulting from the first crystallizer equilibrates at a flow rate of 555 g/h of drained and dried crystals with a purity of 99.95% measured by GC. The overall crystallization yield relative to the continuous feed stream of crude isosorbide distillate is equal to 88.1% by mass.

Like the previous example, this example demonstrates that the process according to the invention adapts perfectly to a continuous operation, which is an asset in terms of cost-effectiveness of an industrial process.

The invention claimed is:

1. A process for producing 1,4:3,6-dianhydrohexitol crystals, comprising:
   a) obtaining a solution of an internal dehydration product of at least one hexitol,
   b) distilling the solution resulting from step a) so as to obtain a solution of at least one 1,4:3,6-dianhydrohexitol,
   c) crystallizing the 1,4:3,6-dianhydrohexitol resulting from step b),
   d) draining the 1,4:3,6-dianhydrohexitol crystals resulting from step c), which results in a crystal-rich stream (1) and a mother liquor stream (1 bis),
   and wherein all or part of the mother liquor stream (1 bis) undergoes an evaporative crystallization step e) in the presence of a solvent, which results in the formation of a solvent stream (2) and in the formation of a stream rich in 1,4:3,6-dianhydrohexitol crystals (2 bis).

2. The process as claimed in claim 1, wherein all of the mother liquor stream (1 bis) resulting from the draining step d) undergoes an evaporative crystallization step e).

3. The process as claimed in claim 1, wherein a part of the mother liquor stream (1 bis) resulting from the draining step d) undergoes an evaporative crystallization step e), from 50% to 99.9% by weight of the stream undergoing the evaporative crystallization step, and from 0.1% to 50% by weight of the stream being reintroduced into the distillate at the crystallization step c).

4. The process as claimed in claim 1, wherein the solvent in the evaporative crystallization step e) is chosen from a $C_1$-$C_4$ linear or branched aliphatic alcohol.

5. The process as claimed in claim 1, wherein the crystals of the stream rich in 1,4:3,6-dianhydrohexitol crystals (2 bis) resulting from the evaporative crystallization step e) are drained at a step f), which results in the formation, on the one hand, of a main stream (3) rich in 1,4:3,6-dianhydrohexitol crystals and, on the other hand, in the formation of a mother liquor stream (3 bis).

6. The process as claimed in claim 5, wherein this main stream (3) rich in 1,4:3,6-dianhydrohexitol crystals is reintroduced into the distillate at step c).

7. The process as claimed in claim 5, wherein the crystals of the main stream (3) are recovered.

8. The process as claimed in claim 5, wherein the mother liquor stream (3 bis) is reintroduced at the evaporative crystallization step e).

9. The process as claimed in claim 5, wherein the mother liquor stream (3 bis) is reintroduced at step a) of providing the starting solution of the internal dehydration product of the hexitol and/or at step b) of distilling the solution of the internal dehydration product of the hexitol, after having removed therefrom the crystallization solvent.

10. The process as claimed in claim 1, wherein the entire process is carried out continuously.

11. The process as claimed in claim 1, wherein the hexitol is chosen from sorbitol, mannitol and iditol, and mixtures thereof.

12. The process as claimed in claim 1, wherein the 1,4:3,6-dianhydrohexitol is isosorbide, isomannide, isoidide or mixtures thereof.

* * * * *